United States Patent
Sharifian et al.

[11] Patent Number: 6,165,341
[45] Date of Patent: Dec. 26, 2000

[54] CATALYTIC FILM, METHODS OF MAKING THE CATALYTIC FILMS, AND ELECTROSYNTHESIS OF COMPOUNDS USING THE CATALYTIC FILM

[75] Inventors: Hossein Sharifian; Allen J. Bard, both of Austin, Tex.

[73] Assignee: Sachem, Inc., Austin, Tex.

[21] Appl. No.: 09/133,850

[22] Filed: Aug. 13, 1998

[51] Int. Cl.[7] .............................. C25D 3/00; C25B 3/00
[52] U.S. Cl. .................. 205/234; 205/345; 205/347; 205/433; 205/437
[58] Field of Search .................................. 205/345, 431, 205/432, 316, 317, 459, 460, 347, 234; 204/290 R, 290 F; 502/162, 200, 201; 437/433

[56] References Cited

U.S. PATENT DOCUMENTS

| | | | |
|---|---|---|---|
| 3,417,003 | 12/1968 | Ross et al. | 205/235 |
| 3,686,079 | 8/1972 | Masunaga et al. | 205/235 |
| 3,767,758 | 10/1973 | Mars et al. | 423/302 |
| 3,978,095 | 8/1976 | Grelat | 260/378 |
| 4,321,313 | 3/1982 | Langer et al. | 429/13 |
| 4,624,755 | 11/1986 | McManis, II et al. | 205/234 |
| 4,645,579 | 2/1987 | Weiss et al. | 204/182.4 |
| 4,818,353 | 4/1989 | Langer et al. | 204/74 |
| 4,849,073 | 7/1989 | Dotson et al. | 204/101 |
| 4,968,394 | 11/1990 | Dotson et al. | 204/101 |
| 5,281,311 | 1/1994 | Sharifian et al. | 204/101 |
| 5,477,610 | 12/1995 | Sharifian | 204/101 |
| 5,965,062 | 10/1999 | Sakata et al. | 252/500 |
| 5,977,241 | 11/1999 | Koloski et al. | 524/502 |

FOREIGN PATENT DOCUMENTS

| | | |
|---|---|---|
| 2602802 | 2/1988 | France. |
| 4428255A1 | 8/1994 | Germany. |
| 04021507 | 1/1992 | Japan. |

OTHER PUBLICATIONS

Colucci et al., "The Electro Reduction Of Nitric Oxide On Bulk Platinum In Acid Solutions", Electrochimica Acta, vol. 30, No. 4, (1985), pp. 521–528. No date available.

Bathia et al., "Hydroxylamine Production By Electroreduction Of Nitric Oxide In A Trickle Bed Cell", The Canadian Journal of Chemical Engineering, vol. 57, No. 5 (Oct. 1979), pp. 631–637.

*Primary Examiner*—Donald R. Valentine
*Attorney, Agent, or Firm*—Renner, Otto, Boisselle & Sklar, LLP

[57] ABSTRACT

In one embodiment, the present invention relates to a method of making a catalytic film comprising: applying an electric current to an electrochemical cell comprising an anode, a cathode and a solution comprising a film forming compound and a nitrate ion source thereby forming the catalytic film.

13 Claims, 2 Drawing Sheets

CATALYTIC FILM, METHODS OF MAKING THE CATALYTIC FILMS, AND ELECTROSYNTHESIS OF COMPOUNDS USING THE CATALYTIC FILM

TECHNICAL FIELD

The present invention relates to a catalytic film, methods of making the catalytic film, and methods of using the catalytic film. More particularly, the invention relates to a catalytic film formed on an electrode from the interaction of a film forming compound and nitrate ions.

BACKGROUND OF THE INVENTION

Hydroxylammonium salts are compounds which have a variety of applications. For instance, hydroxylammonium nitrate may be used as a component of liquid propellant and as a reducing agent in photographic operations. In some of these applications, it is desirable that a hydroxylammonium salt solution of high purity is available.

There exist several production methods to manufacture hydroxylammonium salts. In the case of hydroxylammonium nitrate for example, some of these methods include: electrodialysis of hydroxylammonium chloride and nitrate; reaction of hydroxylammonium sulfate and barium nitrate; three-step cation exchange process employing hydroxylammonium sulfate and nitric acid; and electrolytic reduction of nitric acid. Some of these methods, however, do not provide hydroxylammonium salt solutions of high purity which some applications of the compound require. As a result, procedures have been developed to purify the hydroxylammonium salt solutions produced by existing methods. Nevertheless, there remains a substantial demand for large quantities of high purity hydroxylammonium salt solutions. There also is a demand for an efficient process of making hydroxylammonium salts.

Hydroxylamine is useful as an intermediary in chemical processes especially in the pharmaceutical and agricultural industries. It is also useful in stripper formulations. Stripper formulations may be used to remove photoresists from or clean a substrate. For example, hydroxylamine stripper solutions are used to remove polyamide coatings from metal foil. Hydroxylamine stripper solutions are utilized in the printed circuit board and semiconductor industries.

Frequently, solutions of hydroxylamine, especially solutions prepared from hydroxylammonium salts, contain undesirable amounts of impurities such as salts, ammonium ions, metals and organic materials. Thus, there exists a need for hydroxylamine solutions having high purity. There also is a demand for an efficient process of making hydroxylamine.

The production of hydroxylamine by the electroreduction of nitric oxide in sulfuric acid is described by L. J. J. Janssen et al in *Electrochimica Acta*, 1977, Vol. 22, pp. 27–30 and by M. L. Bathia et al in *The Canadian Journal of Chemical Engineering*, Vol. 57, October 1979, pp. 631–7. Janssen et al utilize a platinum cathode, and Bathia et al utilize a cathode bed of tungsten carbide particles. The electroreduction of nitric oxide on bulk platinum in perchloric acid and sulfuric acid solutions is described by J. A. Colucci et al in *Electrochimica Acta*, Vol. 30, No. 4, pp. 521–528, 1985.

U.S. Pat. No. 5,281,311 relates to a process in an electrolysis cell involving (A) providing an electrolysis cell containing an anolyte compartment containing an anode, a catholyte compartment containing an oxygen-consuming cathode and an anionic divider separating the anolyte and catholyte compartments; (B) providing an aqueous solution containing an acid and water to the anolyte compartment, and an aqueous solution containing hydroxylamine salt, water and optionally, an acid to the catholyte compartment; (C) charging an oxygen-containing gas to the catholyte compartment; (D) passing a direct current through the electrolysis cell for a period of time effective to reduce the acid content in the catholyte compartment and/or to convert the salt to a hydroxylamine; and (E) recovering a hydroxylamine or a hydroxylamine salt solution containing a reduced amount of acid from the catholyte compartment.

U.S. Pat. No. 5,447,610 relates to preparing hydroxylamine and hydroxylammonium salts by electrolytically reducing a mixture containing at least one nitrogen oxide and either a neutral electrolyte to form hydroxylamine or an acidic electrolyte such as an organic or inorganic acid to form a hydroxylammonium salt. The electrolytic reduction is conducted in an electrolysis cell containing an anolyte compartment containing an anode, a catholyte compartment containing a cathode, and a divider separating the anolyte and catholyte compartments where the mixture of at least one nitrogen oxide and the electrolyte is present in the catholyte compartment, and an acid is present in the anolyte compartment.

SUMMARY OF THE INVENTION

In one embodiment, the present invention relates to a catalytic film made by applying an electric current to an electrochemical cell comprising two electrodes and a solution comprising a film forming compound and a nitrate ion source.

In another embodiment, the present invention relates to a method of making a catalytic film comprising: applying an electric current to an electrochemical cell comprising an anode, a cathode and a solution comprising a film forming compound and a nitrate ion source thereby forming the catalytic film.

In yet another embodiment, the present invention relates to a method of using a catalytic film formed on a cathode made by applying an electric current to a first electrochemical cell comprising an anode and the cathode and a film forming solution comprising a film forming compound and a nitrate ion source, comprising: providing a second electrochemical cell comprising an anode, the cathode having the catalytic film, and a reactant solution comprising reactants; applying an electric current to the second electrochemical cell; and recovering a product from the second electrochemical cell.

The present invention provides inexpensive and uncomplicated electrochemical methods of efficiently preparing various compounds of high purity including but not limited to hydroxylammonium salts and adiponitrile.

DESCRIPTION OF THE PREFERRED EMBODIMENTS

Figure 1:
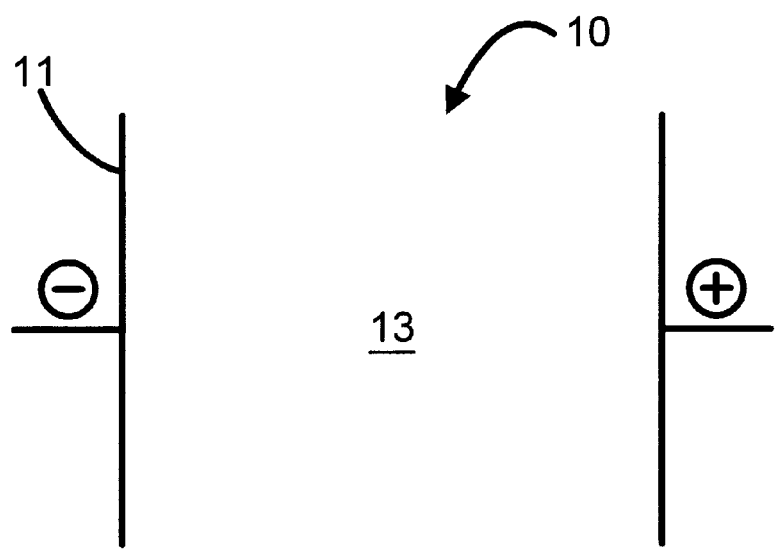
FIG. 1 is a schematic cross-section of an electrochemical cell useful in preparing a catalytic film according to the invention.

In one embodiment, the invention relates to a catalytic film and methods of forming the catalytic film. The catalytic film is formed on an electrode, typically in an electrochemical cell containing at least a cathode, an anode and a solution containing a film forming compound and nitrate ions. In a preferred embodiment, the catalytic film is formed on a cathode of an electrochemical cell.

Although not wishing to be bound by any theory, it is believed that interactions between the film forming compound and nitrate ions form a catalytic film on an electrode. The chemical identity of the catalytic film formed on the electrode due to the presence of a film forming compound is unknown. However, the catalytic film forms substantially uniformly and smoothly over the electrode. The catalytic film typically is dark orange to brown in color. The catalytic film is typically solid versus porous. The film strongly adheres to the electrode. The catalytic film has an apparent catalytic effect of promoting the conversion of at least one of a nitrogen containing compound to a hydroxylammonium salt and acrylonitrile to adiponitrile. Although not wishing to be bound by any theory, it is believed that the catalytic film may increase the overpotential for hydrogen evolution at the cathode thereby promoting the formation of a product, such as hydroxylammonium salts or adiponitrile.

The thickness of the catalytic film formed on the electrode depends upon various conditions such as the length of time that the film forming compound and nitrate ions are permitted to interact, the strength of the electric current, the relative concentrations of the film forming compound and nitrate ions, and other process parameters. The catalytic film typically has a thickness of at least about 0.1 nm, and typically from about 0.1 nm to about 500 µm. In another embodiment, the catalytic film has a thickness of at least about 0.5 nm, and typically from about 0.5 nm to about 100 µm. In another embodiment, the catalytic film has a thickness of at least about 1 nm, and typically from about 1 nm to about 10 µm.

The catalytic film forms fairly rapidly during the first hour of applied electric current, and may last (retain apparent catalytic effect) for at least 3 months. In this connection, once an electrode (such as a cathode) has such a catalytic film formed thereon, it is not necessary to include a film forming compound in the solutions charged to the electrochemical cell for chemical processing. In other words, when an electrochemical cell containing an electrode with such a catalytic film thereon is emptied, the solution recharged to cell need only contain the reactants for producing a desired compound.

Film forming compounds include one or more aromatic compounds and heterocyclic compounds capable of forming a catalytic film in the presence of nitrate ions. Preferred film forming compounds include amino-aromatic compounds and quinone compounds. Specific examples of film forming compounds include 1,4-phenylenediamine; 1,3-phenylenediamine; tetracyanoquinodimethane; N,N,N',N'-tetramethyl-p-phenylenediamine; aminophenols such as p-aminophenol, m-aminophenol and o-aminophenol; aminothiophenols; tetrathiafulvalene; thianthrene; tri-N-p-tolyamine; ferrocene; methylviologen dichloride hydrate; quinone compounds such as hydroquinone, aminoanthraquinones, aminoanthraquinone-2-sulfonic acid sodium salt, anthraquinone-1,5-disulfonic acid disodium salt, and anthraquinone-2,6-disulfonic acid disodium salt; aniline compounds such as acetanilide, 4-bromo-2,3,5,6-tetrafluoroaniline, 4,4'-oxydianiline, and 4'-aminoacetanilide; 1,10-phenanthroline; phenazine; 1,8-diaminonaphthalene; 1,4-diacetylbenzene; terephthaldicarboxaldehyde; terephthalic acid; and 2,5-dichloro-1,4-phenylenediamine.

Determination of whether a prospective compound may be classified as a film forming compound involves assessing whether a film formed by the prospective compound in accordance with the invention promotes the conversion of a reactant compound into a desired compound. In one embodiment, the prospective compound may be classified as a film forming compound if it forms a catalytic film and promotes the conversion of a reactant to a product at a rate faster than the conversion under the same conditions except that the catalytic film is not used. In another embodiment, the prospective compound may be classified as a film forming compound if it forms a catalytic film and promotes the conversion of a nitrogen containing compound to a hydroxylammonium salt at a rate faster than the conversion under the same conditions except that the catalytic film is not used. In yet another embodiment, the prospective compound may be classified as a film forming compound if it forms a catalytic film and promotes the conversion of acrylonitrile to adiponitrile at a rate faster than the conversion under the same conditions except that the catalytic film is not used.

Nitrate ions may be obtained from one or more nitrate ion sources. Sources of nitrate ions include nitric acid, alkali metal nitrates such as sodium nitrate, potassium nitrate and rubidium nitrate, alkaline earth metal nitrates such as magnesium nitrate, calcium nitrate and strontium nitrate, transition metal nitrates such as copper nitrate, nickel nitrate, manganese nitrate, silver nitrate, zinc nitrate, etc., ammonium nitrate, quaternary ammonium nitrates such as tetramethylammonium nitrate, tetraethylammonium nitrate, tetrapropylammonium nitrate, tetrabutylammonium nitrate, tetra-n-octylammonium nitrate, methyltriethylammonium nitrate, diethyidimethylammonium nitrate, methyltripropylammonium nitrate, methyltributylammonium nitrate, cetyltrimethylammonium nitrate, trimethylhydroxyethylammonium nitrate, trimethylmethoxyethylammonium nitrate, dimethyldihydroxyethylammonium nitrate, methyltrihydroxyethylammonium nitrate, phenyltrimethylammonium nitrate, phenyltriethylammonium nitrate, benzyltrimethylammonium nitrate, and benzyltriethylammonium nitrate, quaternary phosphonium nitrates such as tetramethylphosphonium nitrate, tetraethylphosphonium nitrate, tetrapropylphosphonium nitrate, tetrabutylphosphonium nitrate, trimethylhydroxyethylphosphonium nitrate, dimethyidihydroxyethylphosphonium nitrate, methyltrihydroxyethylphosphonium nitrate, phenyltrimethyl phosphonium nitrate, phenyltriethylphosphonium nitrate and benzyltrimethylphosphonium nitrate, and tertiary sulfonium nitrates such as trimethylsulfonium nitrate, triethylsulfonium nitrate, tripropylsulfonium nitrate, and combinations thereof.

Once the catalytic film is formed on an electrode, typically the cathode, the electrochemical cell may be emptied, and solutions containing the reactants of a desired chemical reaction charged to the cell. Alternatively, the catalytic film coated electrode may be removed from the cell and transferred to another electrochemical cell where the desired chemical reaction is carried out.

The electrochemical cells suitable for preparing the catalytic film can assume a number of different configurations. In one embodiment, the electrochemical cell contains at least one compartment including an anode and a cathode (see FIG. 1). In a preferred embodiment, the electrochemical cell contains at least two compartments including an anode, a cathode and a divider (see FIG. 2). In another embodiment, the electrochemical cell contains at least three compartments including an anode, a cathode, a bipolar membrane and a divider (see FIG. 3).

General speaking, the electrochemical cells may be composed of cell materials which are compatible with the materials being charged into the cells. The cell materials must be particularly able to tolerate an acidic environment and sometimes a basic environment.

The cells may be adapted to operate at atmospheric pressure or at elevated pressures. In one embodiment the cell is one capable of operating at elevated pressures of at least about 1 psig up to about 10 psig or higher. Since the anode and cathode do not directly enter into the reaction, they also may be made from a variety of materials that do not react with the solutions added to the cells or the catalytic films formed in the cells.

Suitable cathodes may comprise carbon such as graphite, stainless steel, glassy carbon, titanium, titanium oxide ceramic, niobium, tungsten carbide, silver, lead, chromium, zinc, mercury, manganese dioxide or platinum. For example, the cathode may comprise tungsten carbide, platinum on carbon, silver on carbon, manganese dioxide on carbon, or a platinized titanium. Graphite or carbon felt may be used with the cathode to increase the active surface area of the cathode. Cathodes under the trade designation Ebonex® may also be used.

In some embodiments, a gas is introduced into an electrochemical cell and the cathode is a gas diffusion cathode. The gas-diffusion cathode may comprise a conventional cathode structure formed of a suitable porous hydrophobic material such as polytetrafluoroethylene (PTFE), mixed with carbon black and an optional catalyst. Commercially available gas diffusion cathodes include an ELAT type gas diffusion cathode having an integrated stainless steel mesh current collector with an alloy of PtCo on a hydrophobic PTFE containing Vulcan XC-72 carbon and an EFCG type gas diffusion cathode having an integrated stainless steel mesh current collector with an alloy of PtCo on a Toray carbon substrate.

Various materials can be used as anodes in the electrochemical cells. For example, the anode may be made of metals such as coated titanium electrodes, tantalum, zirconium, hafnium or alloys of the same. Generally, the anodes will have a non-passivable and catalytic film which may comprise metallic noble metals such as platinum, iridium, rhodium, ruthenium or alloys thereof, or a mixture of electroconductive oxides containing at least one oxide or mixed oxides of a noble metal such as platinum, iridium, ruthenium, palladium or rhodium. In one embodiment, the anode is a dimensionally stable anode such as an anode having a titanium base with ruthenium and/or iridium oxides thereon.

Most of the electrochemical cells utilized in making and using the catalytic film of the present invention contain at least one divider or separator, such as ionic or nonionic selective membranes. The dividers and/or bipolar membranes function as diffusion barriers and/or gas separators.

In one embodiment, the dividers or separators which can be utilized in the present invention can be selected from a wide variety of microporous diffusion barriers, screens, filters, diaphragms, etc., which contain pores of the desired size allow anions and/or cations of various chemical compounds to migrate toward one of the electrodes. The microporous dividers can be prepared from various materials including plastics such as polyethylene, polypropylene and Teflon, ceramics, etc. Microporous dividers such as nonionic dividers can be used, for example, in addition to the dividers listed in the Figures. Specific examples of commercially available microporous separators include: Celanese Celgard and Norton Zitex.

In one embodiment, the divider is an anion selective membrane. Any anion selective membrane may be utilized including membranes used in processes for the desalination of brackish water. Preferably, anion selective membranes should be selective with respect to the particular anions present in the cell (e.g., nitrate and halide ions). The preparation and structure of anionic membranes are described in the chapter entitled "Membrane Technology" in *Encyclopedia of Chemical Technology*, Kirk-Othmer, Third Ed., Vol. 15, pp. 92–131, Wiley & Sons, New York, 1985. These pages are hereby incorporated by reference for their disclosure of various anionic membranes which may be useful in the process of the present invention.

Among the anion selective membranes which may be utilized and which are commercially available are the following: AMFLON, Series 310, based on fluorinated polymer substituted with quaternary ammonium groups produced by American Machine and Foundry Company; IONAC MA 3148, MA 3236 and MA 3475, based on polymer substituted with quaternary ammonium derived from heterogenous polyvinylchloride produced by Ritter-Pfaulder Corp., Permutit Division; Tosflex IE-SF 34 or IE-SA 48 made by Tosoh Corp. which is a membrane designed to be stable in alkaline media; NEOSEPTA AMH, NEOSEPTA ACM, NEOSEPTA AFN or NEOSEPTA ACLE-SP from Tokuyama Soda Co.; and Selemion AMV and Selemion AAV from Asahi Glass.

In one embodiment, the divider is a cation selective membrane. The cation selective membranes used in the cells and the process of the invention may be any of those which have been used in the electrochemical purification or recycling of chemical compounds. Preferably, the cation-exchange membranes should contain a highly durable material such as the membranes based on the fluorocarbon series, or from less expensive materials of the polystyrene or polypropylene series. Preferably, however, the cation selective membranes useful in the present invention include fluorinated membranes containing cation selective groups such as perfluorosulfonic acid and perfluorosulfonic and/perfluorocarboxylic acid, perfluorocarbon polymer membranes such as sold by the E. I. dupont Nemours & Co. under the general trade designation "Nafion" such as DuPont's Cationic Nafion 423 and 902 membrane. Other suitable cation selective membranes include styrenedivinyl benzene copolymer membranes containing cation selective groups such as sulfonate groups, carboxylate groups, etc. Raipore Cationic R1010, (from Pall RAI), and NEOSEPTA CMH and NEOSEPTA CM1 membranes from Tokuyama Soda are useful particularly with the higher molecular compounds. The preparation and structure of cation selective membranes are described in the chapter entitled "Membrane Technology" in *Encyclopedia of Chemical Technology*, Kirk-Othmer, Third Ed., Vol. 15, pp. 92–131, Wiley & Sons, New York, 1985. These pages are hereby incorporated by reference for their disclosure of various cation selective membranes which can be useful in the present invention.

The bipolar membranes used in the electrochemical cells are composite membranes containing three parts: a cation selective side or region, an anion selective side or region, and an interface between the two regions. When a direct current passes across a bipolar membrane, with the cation selective side toward or facing the cathode, electrical conduction is achieved by the transport of $H^+$ and $OH^-$ ions which are produced by the dissociation of water which occurs at the interface under the influence of an electrical field. Bipolar membranes are described, for example, in U.S. Pat. Nos. 2,829,095, 4,024,043 (single film bipolar membranes) and in 4,116,889 (cast bipolar membranes). The bipolar membranes useful in the present invention include NEOSEPTA BIPOLAR 1 by Tokuyama Soda, WSI BIPOLAR, and Aqualytics Bipolar membranes.

In one embodiment, the electrochemical cells contain at least one compartment. In a preferred embodiment, the electrochemical cells contain at least two compartments; namely, a catholyte compartment and an anolyte compartment. In another embodiment, the electrochemical cells contain at least three compartments; namely, a catholyte compartment, an anolyte compartment and another compartment such as a buffer compartment, a pass compartment, a base compartment, an acid compartment, and the like. Buffer compartments typically are positioned between two bipolar membranes or a bipolar membrane and an electrode. A pass compartment is typically positioned between two cation selective membranes or two anion selective membranes and serve to further purify the final product. Bases and acids are typically formed in the base compartment and acid compartment, respectively.

The catholyte compartment (or the compartment of a one compartment cell) of the electrochemical cells (generally next to the cathode) contains a solution of a film forming compound and nitrate ions. Aqueous solutions are preferred. In one embodiment, the concentration of the film forming compound may be from about 1 mM to about 1 M. In another embodiment, the film forming compound concentration is from about 5 mM to about 500 mM. In yet another embodiment, the film forming compound concentration is from about 10 mM to about 100 mM. In one embodiment, the concentration of the nitrate ion source may be from about 0.001 M to about 10 M. In another embodiment, the nitrate ion source concentration is from about 0.01 M to about 1 M. In yet another embodiment, the nitrate ion source concentration is from about 0.1 M to about 0.5 M.

The anolyte compartment as well as the remaining compartments, if present, of the electrochemical cells (generally next to the anode) contain a solution of an ionic compound (an electrolyte solution). An ionic compound is any compound that fully or partially ionizes in solution. Ionic compounds include acids, bases, and salts. Aqueous solutions are preferred. The ionic compound in the anolyte compartment may be the same or different from the ionic compound in any other compartment. Any suitable ionic compound can be used in the anolyte and other compartments, but in a preferred embodiment, the ionic compound in the anolyte and other compartments is an acid or a nitrate ion source. The concentration of the ionic compound in the anolyte and other compartment is from about 0.1 M to about 10 M, and preferably from about 2 M to about 6 M. The concentration of the ionic compound in the anolyte compartment may be the same, higher or lower than the concentration of the ionic compound in the other compartments.

The electric current applied between the anode and cathode depends upon how many, if any, dividers are positioned between the anode and cathode and the concentrations of components. In one embodiment, a current density is applied between the anode and cathode with an apparent current density of about 0.01 ASI (amps per square inch) to about 10 ASI, more often from about 1 ASI to 5 ASI at about 1 volt to about 10 volts and about 2 volts to about 5 volts, respectively. The current is applied to the electrochemical cell for a period of time effective to produce the catalytic film on the cathode in the catholyte compartment (or the compartment of a one compartment cell) at a desired thickness.

The electrochemical cell may be maintained at a temperature suitable for the production of the catalytic film. The temperature is typically from about −20° C. to about 70° C. In another embodiment, the temperature is from about 1° C. to about 30° C. Formation of the catalytic film may be monitored by visual observation.

Examples of electrochemical cells useful in the present invention are discussed below and shown in FIGS. 1, 2 and 3.

Referring to FIG. 1, the electrochemical cell 10 is made of a cathode 11 and an anode 12. The electrochemical cell 10 contains one compartment 13. In operation of the electrochemical cell illustrated in FIG. 1, a solution containing a film forming compound and a nitrate ion source is charged to the compartment 13. An electrical potential is established and maintained between the anode and the cathode to produce a flow of current across the electrochemical cell whereupon a catalytic film is produced on the cathode 11 in the compartment 13.

Figure 2:
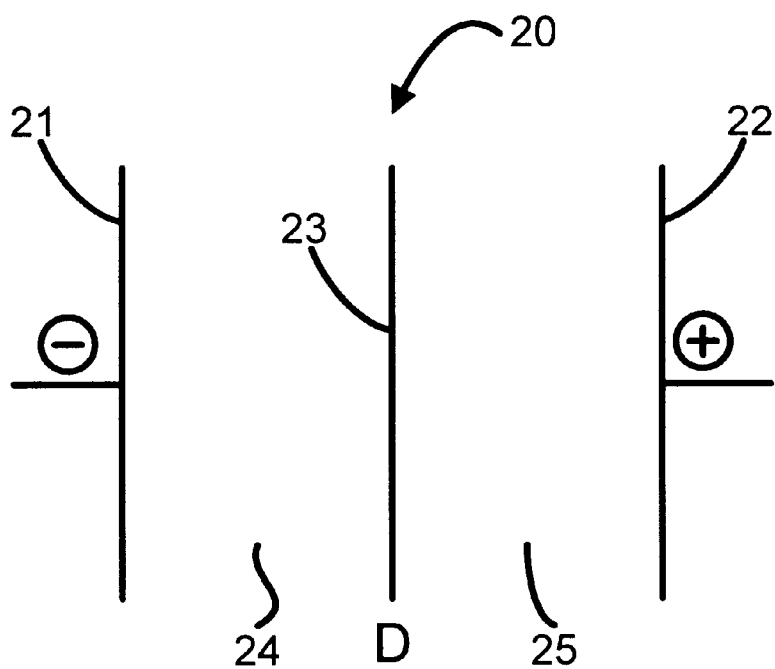
FIG. 2 is a schematic cross-section of an electrochemical cell useful in preparing a catalytic film according to the invention.

Referring to FIG. 2, the electrochemical cell 20 is made of a cathode 21, an anode 22, and a divider 23. The electrochemical cell 20 contains two compartments; namely, a catholyte compartment 24 and an anolyte compartment 25. In operation of the electrochemical cell illustrated in FIG. 2, a solution containing a film forming compound and a nitrate ion source is charged to the catholyte compartment 24. An electrolyte solution containing an ionic compound is charged to the anolyte compartment 25. An electrical potential is established and maintained between the anode and the cathode to produce a flow of current across the electrochemical cell whereupon a catalytic film is produced on the cathode 21 in the catholyte compartment 24.

Figure 3:
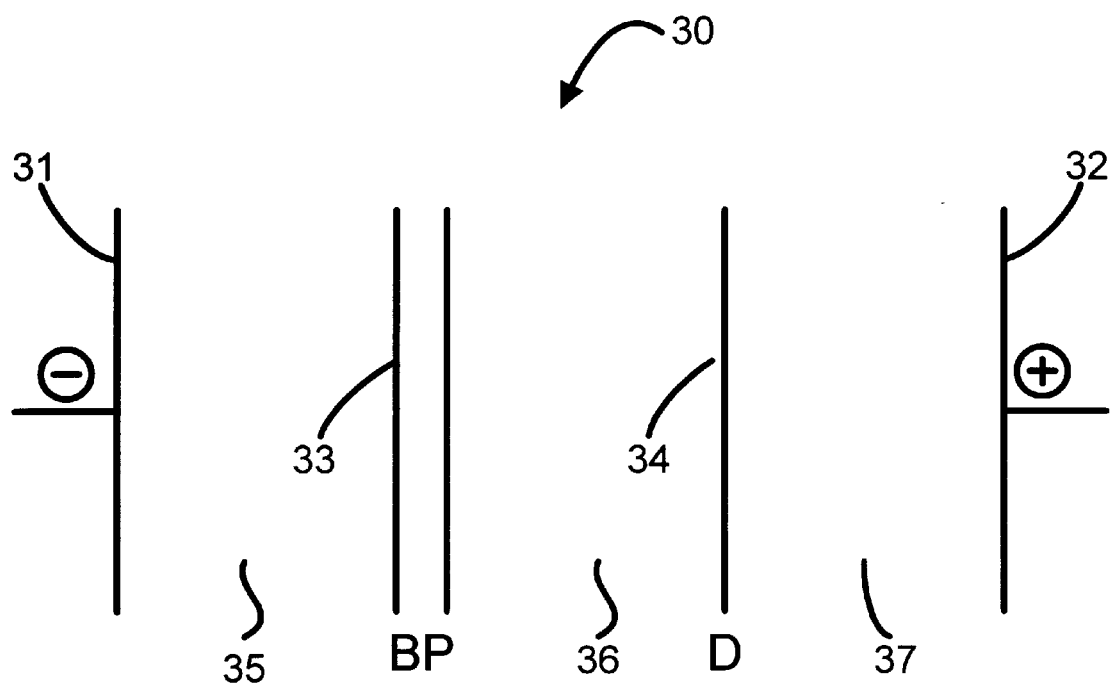
FIG. 3 is a schematic cross-section of an electrochemical cell useful in preparing a catalytic film according to the invention.

Referring to FIG. 3, the electrochemical cell 30 is made of a cathode 31, an anode 32, and in sequence beginning at the cathode 31, a bipolar membrane 33 and a divider 34. The bipolar membrane 33 has an anion selective side (not shown) facing the anode and a cation selective side (not shown) facing the cathode. The electrochemical cell 30 contains three compartments; namely, a catholyte compartment 35, a middle compartment 36, and an anolyte compartment 37. In operation of the electrochemical cell illustrated in FIG. 3, a solution containing a film forming compound and a nitrate ion source is charged to the catholyte compartment 35. A solution containing an ionic compound is charged to the middle compartment 36 and the anolyte compartment 37. The ionic compound of the middle compartment is the same or different than the ionic compound in the anolyte compartment. An electrical potential is established and maintained between the anode and the cathode to produce a flow of current across the electrochemical cell whereupon a catalytic film is produced on the cathode 31 in the catholyte compartment 35.

The following specific examples further illustrate the preparation of the catalytic film according to the present invention. Unless otherwise indicated in the examples and elsewhere in the specification and claims, all parts and percentages are by weight, temperatures are in degrees centigrade, and pressures are at or near atmospheric pressure.

EXAMPLE 1

An electrochemical cell according to FIG. 2 is provided containing an anode made of ruthenium oxide coated titanium, a cathode made of graphite, and a Nafion 423 cation selective membrane as the divider. A solution containing 1 M nitric acid and 50 mM 1,4-phenylenediamine is charged to the catholyte compartment. A solution of 4 M nitric acid is charged to the anolyte compartment. Nitric acid is added to the catholyte compartment to maintain the nitric acid concentration between 0.5 M and 1 M under application of an electrical current. While maintaining the temperature between 5° C. and 10° C., a current of 5 Amps (0.3 ASI) and a cell voltage of about 3.5 volts is applied for 6 hours. The catholyte is stirred under application of the current. A deep orange to brown colored film uniformly forms over the cathode.

EXAMPLE 2

An electrochemical cell according to FIG. 3 is provided containing an anode made of ruthenium oxide coated titanium, a stainless steel cathode, a Tokuyama Bipolar 1 bipolar membrane, a Asahi glass AAV anion selective membrane as the divider. A solution of 0.5 M nitric acid is charged to the middle compartment, a solution of 0.3 M nitric acid is charged to the anolyte compartment, and a solution of 1.7 M hydroxylamine nitrate, 0.7 M nitric acid and 50 mM of 1,4-phenylenediamine is charged to the catholyte compartment. While maintaining the temperature between 5° C. and 10° C., a current of 5 Amps and a cell voltage of about 9.1 volts is applied for 2 hours. The catholyte is stirred under application of the current. A deep orange to brown colored film uniformly forms over the cathode.

EXAMPLE 3

An electrochemical cell according to FIG. 2 is provided containing an anode made of ruthenium oxide coated titanium, a cathode made of graphite, and a Nafion 423 cation selective membrane as the divider. Graphite felt is attached to the graphite cathode to enhance the active cathode surface area. A solution containing 1 M nitric acid and 50 mM to 100 mM anthraquinone-2,6-disulfonic acid disodium salt is charged to the catholyte compartment. A solution of 4 M nitric acid is charged to the anolyte compartment. Nitric acid is added to the catholyte compartment to maintain the nitric acid concentration between 0.5 M and 1 M under application of an electrical current. While maintaining the temperature between 5° C. and 10° C., a current of 15 Amps (1 ASI) and a cell voltage of about 3.5 volts is applied for 24 hours. The catholyte is stirred under application of the current. A deep orange to brown colored film uniformly forms over the cathode.

EXAMPLE 4

An electrochemical cell according to FIG. 2 is provided containing an anode made of ruthenium oxide coated titanium, a cathode made of graphite, and a Nafion 423 cation selective membrane as the divider. Graphite felt is attached to the graphite cathode to enhance the active cathode surface area. A solution containing 1 M nitric acid and 50 mM to 400 mM 4,4'-oxydianiline is charged to the catholyte compartment. A solution of 4 M nitric acid is charged to the anolyte compartment. Nitric acid is added to the catholyte compartment to maintain the nitric acid concentration between 0.5 M and 1 M under application of an electrical current. While maintaining the temperature between 5° C. and 10° C., a current of 30 Amps (2 ASI) and a cell voltage of about 6 volts is applied for 8 hours. The catholyte is stirred under application of the current. A deep orange to brown colored film uniformly forms over the cathode.

EXAMPLE 5

The general procedure of Example 1 is repeated except that a piece of graphite felt is attached to the graphite cathode to enhance the cathode surface area. A solution containing 0.5 M nitric acid and 50 mM 1,4-phenylenediamine is charged to the catholyte compartment. Concentrated nitric acid is added to the catholyte compartment to maintain the nitric acid concentration between 0.5 M and 1 M under application of an electrical current. While maintaining the temperature between 5° C. and 10° C., a current of 20 amps (5 ASI) and a cell voltage of about 5.5 volts is applied for 16 hours. The catholyte is stirred under application of the current. A deep orange to brown colored film uniformly forms over the cathode.

EXAMPLE 6

The general procedure of Example 1 is repeated except that a solution containing 1.0 M nitric acid and 70 ppm p-aminophenol is charged to the catholyte compartment. A solution of 4 M nitric acid is charged to the anolyte compartment. Concentrated nitric acid is added to the catholyte compartment to maintain the nitric acid concentration between 0.5 M and 1 M under application of an electrical current. While maintaining the temperature between 5° C. and 10° C., a current of 20 amps (5 ASI) and a cell voltage of about 5 volts is applied for 30 hours. The catholyte is stirred under application of the current. A deep orange to brown colored film uniformly forms over the cathode.

EXAMPLE 7

The general procedure of Example 1 is repeated except that a solution of 1 M nitric acid and 100 ppm hydroquinone is charged to the catholyte compartment. A solution of 4 M nitric acid is charged to the anolyte compartment. Concentrated nitric acid is added to the catholyte compartment to maintain the nitric acid concentration between 0.5 M and 1 M under application of an electrical current. While maintaining the temperature between 5° C. and 10° C., a current of 20 amps (5 ASI) and a cell voltage of about 6.5 volts is applied for 1 hour. The catholyte is stirred under application of the current. A deep orange to brown colored film uniformly forms over the cathode.

EXAMPLE 8

An electrochemical cell according to FIG. 2 is provided containing an anode made of ruthenium oxide coated titanium, a cathode made of graphite, and a Nafion 423 cation selective membrane as the divider. A solution containing 1 M sodium nitrate and 50 mM 1,4-phenylenediamine is charged to the catholyte compartment. A solution of 4 M nitric acid is charged to the anolyte compartment. Nitric acid is added to the catholyte compartment to maintain the sodium nitrate concentration between 0.5 M and 1 M under application of an electrical current. While maintaining the temperature between 5° C. and 10° C., a current of 5 Amps (0.3 ASI) and a cell voltage of about 3.5 volts is applied for 6 hours. The catholyte is stirred under application of the current. A deep orange to brown colored film uniformly forms over the cathode.

EXAMPLE 9

An electrochemical cell according to FIG. 1 is provided containing an anode made of ruthenium oxide coated titanium and a cathode made of graphite. A solution containing 1 M tetrabutylammonium nitrate and 50 mM 1,4-phenylenediamine is charged to the compartment. Nitric acid is added to the compartment to maintain the tetrabutylammonium nitrate concentration between 0.5 M and 1 M under application of an electrical current. While maintaining the temperature between 5° C. and 10° C., a current of 5 Amps (0.3 ASI) and a cell voltage of about 3.5 volts is applied for 6 hours. The compartment is stirred under application of the current. A deep orange to brown colored film uniformly forms over the cathode.

Using the cathode having a catalytic film thereon, the synthesis of various compounds is facilitated. For example, the conversion of a nitrogen containing compound to a hydroxylammonium salt and the conversion of acrylonitrile to adiponitrile are facilitated by the catalytic film of the present invention.

Generally speaking, an electrochemical cell containing an electrode having a catalytic film thereon is used to facilitate the synthesis of various compounds. In a preferred embodiment, the electrode is a cathode. The synthesis of various compounds may be carried out in the electrochemical cell in which the catalytic film is formed, or an electrode on which the catalytic film is formed may be transferred to another electrochemical cell. Any electrochemical cell suitable for the synthesis of a particular compound may be equipped with an electrode having a catalytic film thereon. For example, the electrochemical cells of FIGS. 2 and 3 are suitable for making a hydroxylammonium salt and adiponitrile.

The electrochemical cells can be operated batchwise or in a continuous operation. Circulation is effected by pumping and/or by gas evolution. In one embodiment, the concentration of ionic compound in the catholyte, anolyte and/or recovery compartments is maintained at a substantially constant concentrations by the monitoring and employment of feeds into the compartments, such as a water feed into the anolyte compartment.

In one embodiment of the invention, the catalytic film is used to electrochemically convert a nitrogen containing compound to a hydroxylammonium salt. In particular, the nitrogen containing compound is reduced to a hydroxylammonium salt in the presence of a film formed by the film forming compound on a cathode. Referring to FIG. 2, a solution containing a nitrogen containing compound is charged to the catholyte compartment 24. An electrolyte solution containing an ionic compound is charged to the anolyte compartment 25. In a preferred embodiment, the ionic compound is an acid. In this embodiment, the divider 23 is preferably a cation selective membrane. In some embodiments, additional dividers may be used in the cell, but they are not generally required. An electrical potential is established and maintained between the anode and the cathode to produce a flow of current across the electrochemical cell whereupon a hydroxylammonium salt is produced in the catholyte compartment 24. A hydroxylammonium salt is recovered from the catholyte compartment 24. The hydroxylammonium salt may be purified by further treatment using one or more of distillation, reverse osmosis, electrodialysis and ion exchange techniques.

Ion exchange techniques, using cation exchange resins and anion exchange resins, are known to those skilled in the art. Distillation techniques are known by those skilled in the art. For example, the hydroxylamonium salt solution obtained from the catholyte compartment can be further purified using vacuum distillation.

Reverse osmosis membranes are available from Fluid Systems, Filmtech, Osmonics, Inc., Desalination Systems Inc., and others. Specific examples include Fluid Systems TFCL-HP thin film composite membrane. Reverse osmosis membrane technology is known by those skilled in the art.

For example, the hydroxylamine solution obtained from the catholyte compartment containing hydroxylammonium salts is sent through a reverse osmosis membrane (for instance, polyamide based membrane) under high pressure (over 100 and often over 500 psi). Some compounds pass through the membrane whereas the hydroxylammonium salts do not. Reverse osmosis membranes generally permit water and small molecular weight organics (such as hydroxylamine) to pass through while not permitting ionic compounds to pass.

The hydroxylammonium solution obtained from the catholyte compartment can be further purified using electrodialysis in an electrodialytic cell. Electrodialytic techniques are known by those skilled in the art.

These additional procedures are effective for removing impurities that may be present in the solution obtained from the compartments. The impurities include undesirable salts, ammonium ions, metals and organic materials.

In embodiments where hydroxylammonium salt is produced in the catholyte compartment, a current is applied between the anode and cathode with an apparent current density of about 0.1 ASI (amps per square inch) to about 10 ASI, more often from about 2 ASI to 4 ASI at about 3 volts to about 4 volts. The current is applied to the electrochemical cell for a period of time effective to produce the hydroxylammonium salt in the catholyte compartment.

The concentration of nitrogen containing compound in the catholyte compartment may be from about 0.01 M to about 10 M. Preferably the nitrogen containing compound concentration is from about 0.5 M to about 1 M. The concentration of the ionic compound in the anolyte compartment may be from about 0.01 M to about 5 M. Preferably the acid concentration is from about 0.5 M to about 1 M.

Nitrogen containing compounds are compounds containing at least one atom of nitrogen and which are capable of being converted to a hydroxylammonium salt in accordance with the present invention. Examples of nitrogen containing compounds include nitric acid, alkali metal nitrates such as sodium nitrate and potassium nitrate, alkaline earth metal nitrates such as magnesium nitrate and calcium nitrate, alkali nitrites such as sodium nitrite and potassium nitrite, alkaline earth metal nitrites, nitrides such as calcium nitride and magnesium nitride, organo-nitro compounds such as nitromethane, nitroethane, nitropropane, nitrobutane, nitrobenzene, etc., and nitrogen containing gases.

A nitrogen containing gas as used herein includes any gas containing an atom of nitrogen. Examples of nitrogen containing gas include nitrogen oxide gas and nitrogen-hydrogen gas. Nitrogen oxide gas as used herein is intended to mean a gas containing nitrogen and oxygen atoms. Examples of nitrogen oxide gas include one or more of nitric oxide (NO), nitrogen dioxide ($NO_2$), nitrogen trioxide ($NO_3$), dinitrogen trioxide ($N_2O_3$), dinitrogen pentoxide $N_2O_5$. Nitrogen-hydrogen gas includes ammonia, hydrazine, and derivatives thereof. Nitrogen containing gas may also be any gas containing at least a nitrogen containing gas, for instance, a mixture of one or more inert gases and nitrogen oxide gas. Inert gases include nitrogen and the noble gases.

In embodiments where a gas is introduced into an electrochemical cell, such as a nitrogen containing gas in a process for making a hydroxylammonium salt, the cathode is a gas diffusion cathode. In these embodiments, the electrochemical cell contains a gas chamber next to the gas diffusion cathode. A nitrogen containing gas is injected into the gas chamber and then forced through the gas diffusion cathode into the catholyte compartment. Such methods are described in U.S. Pat. No. 5,447,610 and U.S. patent application Ser. No. 08/734,858, both of which are hereby incorporated by reference. In one embodiment, the cathode may contain a material which exhibits electrocatalytic activity for nitrogen oxide reduction to hydroxylamine or hydroxylammonium salts.

The hydroxylammonium salts which can be produced in the electrochemical cells from nitrogen containing compounds in accordance with the process of the present invention may be represented by the formula $$(NR_2HOH)^+_y X^{-y}$$

wherein each R is independently hydrogen or a hydrocarbon group containing from 1 to about 8 carbon atoms, preferably 1 to about 6 carbon atoms, X is an anion of an acid, such as any of the acids described above, and y is a number equal to the valence of X. Specific examples of anions include $Cl^-$, $Br^-$, $SO_4^{-2}$, $HSO_4^-$, $NO_3^-$, $PO_4^{-3}$, $HPO_4^{-2}$, etc.

Specific examples of hydroxylammonium salts which can be prepared in accordance with this invention include hydroxylammonium sulfate, hydroxylammonium nitrate, hydroxylammonium chloride, hydroxylammonium bromide, hydroxylammonium fluoride, hydroxylammonium formate, hydroxylammonium acetate, hydroxylammonium phosphate, hydroxylammonium methylsulfonate, hydroxylammonium toluene sulfonate, methylhydroxylammonium nitrate, ethylhydroxylammonium nitrate, propylhydroxylammonium nitrate, isopropylhydroxylammonium nitrate, and diethylhydroxylammonium nitrate, phenylhydroxylammonium nitrate, etc.

The concentration of hydroxylammonium salt formed in the catholyte compartment may be from about 0.1 M to about 10 M. Preferably the hydroxylammonium salt concentration in the catholyte compartment is from about 0.5 M to about 2 M.

In one embodiment, the ionic compound is an acid and a solution of the acid is an acidic electrolyte. An acid lowers the pH of a neutral solution. Acids include organic and inorganic acids. Preferably, the acid is not reactive at the cathode.

Specific examples of inorganic acids represented by formula $H_yX$ which may be utilized in the acidic electrolyte with the nitrogen containing compound include at least one of nitric acid, halogen acids such as hydrofluoric acid, hydrochloric acid, hydrobromic acid and hydriodic acid, sulfuric acid, sulfurous acid, perchloric acid, boric acid and phosphorus acids such as phosphorous acid and phosphoric acid. Nitric acid and sulfuric acid are preferred inorganic acids. Nitric acid and any other acid are preferred combinations of acids. Examples of organic acids represented by the formula $H_yX$ include carboxylic and polycarboxylic acids such as formic acid, acetic acid, propionic acid, citric acid, oxalic acid, etc.; organic phosphorus acids such as dimethylphosphoric acid and dimethylphosphinic acid; or sulfonic acids such as methanesulfonic acid, ethanesulfonic acid, 1-pentanesulfonic acid, 1-hexanesulfonic acid, 1-heptanesulfonic acid, benzenesulfonic acid, toluenesulfonic acid, etc. Nitric acid and any other acid are preferred combinations of acids.

In one embodiment, the ionic compound is a base and a solution of the base is a basic electrolyte. A base increases the pH of a neutral solution. Bases include organic and inorganic bases.

Bases include alkali metal and alkaline earth metal hydroxides, silicates, phosphates, borates, carbonates, and mixtures thereof. For example, the basic compound includes alkali metal hydroxides, alkaline earth metal hydroxides, alkali metal silicates and so on. Alkali metals include lithium, sodium, potassium, rubidium and cesium. Alkaline earth metals include beryllium, magnesium, calcium, strontium, and barium. Specific bases include sodium tetraborate, sodium carbonate, sodium bicarbonate, sodium hydroxide, sodium phosphate, sodium pyrophosphate and other polyphosphates, sodium silicate, potassium carbonate, potassium bicarbonate, potassium hydroxide, potassium phosphate, potassium pyrophosphate and other polyphosphates, calcium carbonate, calcium hydroxide, calcium phosphate, calcium pyrophosphate, calcium silicate, magnesium carbonate, magnesium hydroxide, magnesium phosphate, magnesium pyrophosphate, and magnesium silicate.

Examples of electrochemical cells useful in the present invention are discussed below and shown in FIGS. 1, 2 and 3.

As needed, various compounds such as one or more acids, water, one or more ionic compounds, nitrogen containing compounds, stabilizers, hydrogen suppressors and the like may be added or recovered from the catholyte, anolyte and other compartments in order to maintain efficient operation of the electrochemical cell. For example, nitrogen containing compound must be continuously or intermittently added to the catholyte compartment. From time to time, it may also be necessary to intermittently or continuously remove acid from the anolyte compartment.

In one embodiment, the solutions charged to the compartments where a hydroxylammonium salt (or adiponitrile as described below) is produced may also optionally contain a hydrogen suppressor. Hydrogen suppressors include thio compounds such as thiourea, and quaternary ammonium salts such as quaternary alkyl ammonium chlorides, nitrates, sulfates, bromides, phosphates, carbonates and bicarbonates. Specific quaternary alkyl ammonium ions include quaternary methyl ammonium, quaternary ethyl ammonium, quaternary propyl ammonium, quaternary butyl ammonium, dimethyldiethyl ammonium, methyltriethyl ammonium, and so on. In one embodiment, the amount of hydrogen suppressor in the solution may range from about 0.001% to about 10% by weight of the solution. In another embodiment, the amount of hydrogen suppressor in the solution may range from about 0.01% to about 1% by weight of the solution.

In another embodiment, the solutions charged to the compartments where a hydroxylammonium salt is produced may also optionally contain a stabilizer. In some instances, a stabilizer inhibits the decomposition of hydroxylammonium salt. Examples of stabilizers include quinoline derivatives, thiocarboxylic acids, thiosulfates, hydroxy anthraquinone, etc. Specific examples include 8-hydroxyquinoline, morin hydrate and quercetin. The amount of stabilizer in the solution may range from about $5 \times 10^{-4}\%$ to about 1% by weight based on the weight of electrolytes present.

In another embodiment of the invention, the catalytic film is used to electrochemically convert acrylonitrile to adiponitrile. In particular, acrylonitrile is converted to adiponitrile in the presence of a film formed by the film forming compound on a cathode. Referring to FIG. 2, a solution containing acrylonitrile is charged to the catholyte compartment 24. An electrolyte solution containing an ionic compound is charged to the anolyte compartment 25. In a preferred embodiment, the ionic compound is an acid. In this embodiment, the divider 23 is preferably a cation selective membrane. In some embodiments, additional dividers may be used in the cell, but they are not generally required. An electrical potential is established and maintained between the anode and the cathode to produce a flow of current across the electrochemical cell whereupon adiponitrile is produced in the catholyte compartment 24. Adiponitrile is recovered from the catholyte compartment 24. Adiponitrile may be purified by further treatment using one or more of distillation, reverse osmosis, electrodialysis and ion exchange techniques.

In embodiments where adiponitrile is produced in the catholyte compartment, a current is applied between the anode and cathode with an apparent current density of about 0.1 ASI (amps per square inch) to about 10 ASI, more often from about 2 ASI to 4 ASI at about 3 volts to about 4 volts. The current is applied to the electrochemical cell for a period of time effective to produce the adiponitrile in the catholyte compartment.

The concentration of acrylonitrile in the catholyte compartment may be from about 0.01 M to about 10 M. Preferably the acrylonitrile concentration is from about 0.5 M to about 1 M. The concentration of the ionic compound in the anolyte compartment may be from about 0.01 M to about 5 M. Preferably the ionic compound concentration is from about 0.5 M to about 1 M. Ionic compounds are described above.

The concentration of adiponitrile formed in the catholyte compartment may be from about 0.1 M to about 10 M. Preferably the adiponitrile concentration formed in the catholyte compartment is from about 0.5 M to about 2 M.

The following specific examples further illustrate the preparation of the hydroxylammonium salts and hydroxylamine according to the present invention. Unless otherwise indicated in the examples and elsewhere in the specification and claims, all parts and percentages are by weight, temperatures are in degrees centigrade, and pressures are at or near atmospheric pressure.

EXAMPLE 10

An electrochemical cell according to FIG. 2 is provided containing an anode made of ruthenium oxide coated titanium, the cathode made according to Example 1, and a Nafion 423 cation selective membrane as the divider. A solution containing 1 M nitric acid is charged to the catholyte compartment. A solution of 4 M nitric acid is charged to the anolyte compartment. Nitric acid is added to the catholyte compartment to maintain the nitric acid concentration between 0.5 M and 1 M under application of an electrical current. While maintaining the temperature between 5° C. and 10° C., a current of 5 Amps (0.3 ASI) and a cell voltage of about 3.5 volts is applied. The catholyte is stirred under application of the current. A solution of 1.3 M hydroxylammonium nitrate and 0.8 M nitric acid with no detectable ammonium nitrate is obtained from the catholyte compartment. An overall current efficiency of 60% for formation of hydroxylammonium nitrate is achieved.

EXAMPLE 11

An electrochemical cell according to FIG. 2 is provided containing an anode made of ruthenium oxide coated titanium, the cathode made according to Example 3, and a Nafion 423 cation selective membrane as the divider. A solution containing 1 M nitric acid is charged to the catholyte compartment. A solution of 4 M nitric acid is charged to the anolyte compartment. Nitric acid is added to the catholyte compartment to maintain the nitric acid concentration between 0.5 M and 1 M under application of an electrical current. While maintaining the temperature between 5° C. and 10° C., a current of 15 Amps (1 ASI) and a cell voltage of about 3.5 volts is applied. The catholyte is stirred under application of the current. A solution of 1.1 M hydroxylammonium nitrate and 0.9 M nitric acid and 0.05 M ammonium nitrate is obtained from the catholyte compartment. An overall current efficiency of 35% for formation of hydroxylammonium nitrate is achieved.

EXAMPLE 12

An electrochemical cell according to FIG. 2 is provided containing an anode made of ruthenium oxide coated titanium, the cathode made according to Example 4, and a Nafion 423 cation selective membrane as the divider. A solution containing 1 M nitric acid is charged to the catholyte compartment. A solution of 4 M nitric acid is charged to the anolyte compartment. Nitric acid is added to the catholyte compartment to maintain the nitric acid concentration between 0.5 M and 1 M under application of an electrical current. While maintaining the temperature between 5° C. and 10° C., a current of 30 Amps (2 ASI) and a cell voltage of about 6 volts is applied. The catholyte is stirred under application of the current. A solution of 1.9 M hydroxylammonium nitrate and 0.8 M nitric acid with no detectable ammonium nitrate is obtained from the catholyte compartment. An overall current efficiency of 60% for formation of hydroxylammonium nitrate is achieved.

EXAMPLE 13

An electrochemical cell according to FIG. 2 is provided containing an anode made of ruthenium oxide coated titanium, the cathode made according to Example 4, and a Nafion 423 cation selective membrane as the divider. A solution containing 1 M nitric acid is charged to the catholyte compartment. A solution of 4 M nitric acid is charged to the anolyte compartment. Nitric acid is added to the catholyte compartment to maintain the nitric acid concentration between 0.5 M and 1 M under application of an electrical current. While maintaining the temperature between 5° C. and 10° C., a current of 15 Amps (1 ASI) and a cell voltage of about 4.5 volts is applied. The catholyte is stirred under application of the current. A solution of 1.2 M hydroxylammonium nitrate and 1.2 M nitric acid and 0.1 M ammonium nitrate is obtained from the catholyte compartment. An overall current efficiency of 40% for formation of hydroxylammonium nitrate is achieved.

EXAMPLE 14

An electrochemical cell according to FIG. 2 is provided containing an anode made of ruthenium oxide coated titanium, a cathode made of niobium, and a Nafion 423 cation selective membrane as the divider. A solution containing 1 M nitric acid and 50 mM 1,4-phenylenediamine is charged to the catholyte compartment. A solution of 4 M nitric acid is charged to the anolyte compartment. Nitric acid is added to the catholyte compartment to maintain the nitric acid concentration between 0.5 M and 1 M under application of an electrical current. While maintaining the temperature between 5° C. and 10° C., a current of 5 Amps (0.3 ASI) and a cell voltage of about 3 volts is applied. The catholyte is stirred under application of the current. A film forms on the cathode after about 1 hour and a solution of 0.8 M hydroxylammonium nitrate and 0.9 M nitric acid and 0.03 M ammonium nitrate is obtained from the catholyte compartment. An overall current efficiency of 45% for formation of hydroxylammonium nitrate is achieved.

EXAMPLE 15

An electrochemical cell according to FIG. 2 is provided containing an anode made of ruthenium oxide coated titanium, the cathode made according to Example 5, and a Nafion 423 cation selective membrane as the divider. A solution containing 0.5 M nitric acid is charged to the catholyte compartment. Concentrated nitric acid is added to the catholyte compartment to maintain the nitric acid concentration between 0.5 M and 1 M under application of an electrical current. While maintaining the temperature between 5° C. and 10° C., a current of 20 amps (5 ASI) and a cell voltage of about 5.5 volts is applied. The catholyte is stirred under application of the current. A solution of 1.67 M hydroxylammonium nitrate and 0.50 M nitric acid with no detectable ammonium nitrate is obtained from the catholyte compartment. An overall current efficiency of 85% for formation of hydroxylammonium nitrate is achieved.

EXAMPLE 16

An electrochemical cell according to FIG. 2 is provided containing an anode made of ruthenium oxide coated titanium, the cathode made according to Example 6, and a Nafion 423 cation selective membrane as the divider. A solution containing 1.0 M nitric acid is charged to the catholyte compartment. A solution of 4 M nitric acid is charged to the anolyte compartment. Concentrated nitric acid is added to the catholyte compartment to maintain the nitric acid concentration between 0.5 M and 1 M under application of an electrical current. While maintaining the temperature between 5° C. and 10° C., a current of 20 amps (5 ASI) and a cell voltage of about 5 volts is applied. A solution of 1.26 M hydroxylammonium nitrate and 0.7 M nitric acid with no detectable ammonium nitrate is obtained from the catholyte compartment. An overall current efficiency of 74% for formation of hydroxylammonium nitrate is achieved.

EXAMPLE 17

An electrochemical cell according to FIG. 2 is provided containing an anode made of ruthenium oxide coated titanium, the cathode made according to Example 7, and a Nafion 423 cation selective membrane as the divider. A solution of 1 M nitric acid is charged to the catholyte compartment. A solution of 4 M nitric acid is charged to the anolyte compartment. Concentrated nitric acid is added to the catholyte compartment to maintain the nitric acid concentration between 0.5 M and 1 M under application of an electrical current. While maintaining the temperature between 5° C. and 10° C., a current of 20 amps (5 ASI) and a cell voltage of about 6.5 volts is applied. A solution of 1.3 M hydroxylammonium nitrate and 0.8 M nitric acid with no detectable ammonium nitrate is obtained from the catholyte compartment. An overall current efficiency of 60% for formation of hydroxylammonium nitrate is achieved.

EXAMPLE 18

An electrochemical cell according to FIG. 2 is provided containing an anode made of ruthenium oxide coated titanium, the cathode made according to Example 1, and a Nafion 423 cation selective membrane as the divider. A solution of 1 M hydrochloric acid and 1 M nitrobenzene is charged to the catholyte compartment of a cell. A solution of 4 M nitric acid is charged to the anolyte compartment. While maintaining the temperature between 25° C. and 30° C., a current of 10 amps (2.5 ASI) and a cell voltage of about 5.5 volts is applied. The catholyte is stirred under application of the current. A solution of 0.9 M phenylhydroxylammonium chloride is obtained from the catholyte compartment. An overall current efficiency of 55% for formation of phenylhydroxylammonium chloride is achieved.

EXAMPLE 19

An electrochemical cell according to FIG. 2 is provided containing an anode made of ruthenium oxide coated titanium, the cathode made according to Example 1, and a Nafion 423 cation selective membrane as the divider. The general procedure of Example 10 is repeated except that thiourea is also added into the catholyte compartment. A solution of 1 M nitric acid and 250 mM of thiourea is charged to the catholyte compartment. A solution of 4 M nitric acid is charged to the anolyte compartment. Nitric acid is added to the catholyte compartment to maintain the nitric acid concentration between 0.5 M and 1 M under application of an electrical current. While maintaining the temperature between 5° C. and 10° C., a current of 45 amps (3 ASI) and a cell voltage of about 6.5 volts is applied. The catholyte is stirred under application of the current. A solution of 1.77 M hydroxylammonium nitrate and 0.5 M nitric acid with no detectable ammonium nitrate is obtained from the catholyte compartment. An overall current efficiency of 90% for formation of hydroxylammonium nitrate is achieved.

EXAMPLE 20

An electrochemical cell according to FIG. 2 is provided containing an anode made of ruthenium oxide coated titanium, the cathode made according to Example 1, and a Nafion 423 cation selective membrane as the divider. The general procedure of Example 10 is repeated except that tetrabutylammonium chloride is added into the catholyte compartment. A solution of 1 M nitric acid and 0.1 M tetrabutylammonium chloride is charged to the catholyte compartment. A solution of 4 M nitric acid is charged to the anolyte compartment. Nitric acid is added to the catholyte compartment to maintain the nitric acid concentration between 0.5 M and 1 M under application of an electrical current. While maintaining the temperature between 5° C. and 10° C., a current of 45 amps (3 ASI) and a cell voltage of about 6.5 volts is applied. The catholyte is stirred under application of the current. A solution of 1.65 M hydroxylammonium nitrate and 0.7 M nitric acid with no detectable ammonium nitrate is obtained from the catholyte compartment. An overall current efficiency of 85% for formation of hydroxylammonium nitrate is achieved.

EXAMPLE 21

An electrochemical cell according to FIG. 2 is provided containing an anode made of ruthenium oxide coated titanium, the cathode made according to Example 1, and a Nafion 423 cation selective membrane as the divider. The general procedure of Example 10 is repeated except that a solution 1 M nitrobenzene is also charged is added to the catholyte compartment of a cell. A solution of 4 M nitric acid is charged to the anolyte compartment. While maintaining the temperature between 25° C. and 30° C., a current of 10 amps (2.5 ASI) and a cell voltage of about 5.5 volts is applied. The catholyte is stirred under application of the current. A solution of 0.9 M phenylhydroxylammonium nitrate is obtained from the catholyte compartment. An overall current efficiency of 55% for formation of phenylhydroxylammonium nitrate is achieved.

EXAMPLE 22

An electrochemical cell according to FIG. 2 is provided containing an anode made of ruthenium oxide coated titanium, the cathode made according to Example 3, and a Nafion 423 cation selective membrane as the divider.

The general procedure of Example 10 is repeated except that a solution of 1.5 M of acrylonitrile and 0.2 M of tetraethylammonium p-toluenesulfonate is charged to the catholyte compartment. A solution of 4 M nitric acid is charged to the anolyte compartment. While maintaining the temperature between 25° C. and 30° C., a current of 12 amps (3 ASI) and a cell voltage of about 4.50 volts is applied. A solution of 0.45 M adiponitrile is obtained from the catholyte compartment. An overall current efficiency of 95% for formation of adiponitrile is achieved.

The present invention provides efficient, inexpensive and uncomplicated electrochemical methods of preparing hydroxylammonium salts and adiponitrile of high purity. Since the use of mercury containing and/or lead containing cathodes is not required, the present invention does not raise toxicity concerns and is environmentally friendly. Since in some embodiments the use of gas permeable cathodes is not required, the present invention is relatively inexpensive and uncomplicated to practice.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A method of making a catalytic film comprising:
   applying an electric current to an electrochemical cell comprising an anode, a cathode and a solution comprising a film forming compound and a nitrate ion source thereby forming the catalytic film, wherein the catalytic film is formed on the cathode, and
   wherein the film forming compound comprises at least one compound selected from aromatic compounds and heterocyclic compounds capable of forming a catalytic film in the presence of the nitrate ion source.

2. The method according to claim 1, wherein the electrochemical cell further comprises a divider between the anode and cathode.

3. The method according to claim 1, wherein the solution has a temperature from about −20° C. to about 70° C. and the electric current has an apparent current density from about 0.1 ASI to about 10 ASI at about 1 volt to about 10 volts.

4. The method according to claim 1, wherein the solution comprises from about 1 mM to about 1 M of the film forming compound and from about 0.01 M to about 1 M of the nitrate ion source.

5. The method according to claim 1, wherein the solution comprises from about 1 mM to about 1 M of the film forming compound and from about 0.1 M to about 0.5 M of the nitrate ion source.

6. The method according to claim 1, wherein the catalytic film has a thickness from about 0.5 nm to about 100 μm.

7. The method according to claim 1, wherein the film forming compound comprises at least one of 1,4-phenylenediamine; 1,3-phenylenediamine; tetracyanoquinodimethane; N,N,N',N'-tetramethyl-p-phenylenediamine; p-aminophenol; m-aminophenol; o-aminophenol; aminothiophenols; tetrathiafulvalene; thianthrene; tri-N-p-tolyamine; ferrocene; methylviologen dichloride hydrate; hydroquinone; aminoanthraquinones; aminoanthraquinone-2-sulfonic acid sodium salt; anthraquinone-1,5-disulfonic acid disodium salt; anthraquinone-2,6-disulfonic acid disodium salt; acetanilide, 4-bromo-2,3,5,6-tetrafluoroaniline, 4,4'-oxydianiline; 4'-aminoacetanilide; 1,10-phenanthroline; phenazine; 1,8-diaminonaphthalene; 1,4-diacetylbenzene; terephthaldicarboxaldehyde; terephthalic acid; and 2,5-dichloro-1,4-phenylenediamine.

8. A method of using a catalytic film formed on a cathode made by applying an electric current to a first electrochemical cell comprising an anode and the cathode and a film forming solution comprising a film forming compound and a nitrate ion source, comprising:
   providing a second electrochemical cell comprising an anode, the cathode having the catalytic film, and a reactant solution comprising reactants;
   applying an electric current to the second electrochemical cell; and
   recovering a product from the second electrochemical cell.

9. The method according to claim 8, wherein the first electrochemical cell and the second electrochemical cell are the same electrochemical cell.

10. The method according to claim 8, wherein the first electrochemical cell and the second electrochemical cell are different electrochemical cells.

11. The method according to claim 8, wherein the reactants comprise a nitrogen containing compound and the product comprises a hydroxylammonium salt.

12. The method according to claim 8, wherein the reactants comprise acrylonitrile and the product comprises adiponitrile.

13. A method of making a catalytic film comprising:
   applying an electric current to an electrochemical cell comprising an anode, a cathode and a solution comprising a film forming compound and a nitrate ion source thereby forming the catalytic film, wherein the catalytic film is formed on the cathode, and
   wherein the film forming compound and the nitrate ion source are different compounds and the film forming compound is selected from amino-aromatic compounds, quinone compounds or mixtures thereof, and the film forming compound and the nitrate ion source are different compounds.

* * * * *